(12) United States Patent
Gallagher

(10) Patent No.: US 9,554,904 B2
(45) Date of Patent: Jan. 31, 2017

(54) DISTAL TIP ASSEMBLY FOR A HEART VALVE DELIVERY CATHETER

(75) Inventor: John Gallagher, Dublin (IE)

(73) Assignee: Medtronic CV Luxembourg S.a.r.l., Luxembourg (LU)

( * ) Notice: Subject to any disclaimer, the term of this patent is extended or adjusted under 35 U.S.C. 154(b) by 188 days.

(21) Appl. No.: 13/247,315

(22) Filed: Sep. 28, 2011

(65) Prior Publication Data

US 2013/0079872 A1   Mar. 28, 2013

(51) Int. Cl.
*A61F 2/24* (2006.01)
*A61F 2/962* (2013.01)
*A61M 25/00* (2006.01)
*A61M 25/06* (2006.01)

(52) U.S. Cl.
CPC ............ *A61F 2/2436* (2013.01); *A61F 2/962* (2013.01); *A61M 25/0074* (2013.01); *A61M 2025/0687* (2013.01)

(58) Field of Classification Search
CPC ...... A61F 2/2427; A61F 2/243; A61F 2/2433; A61F 2/2436; A61F 2/2439; A61F 2/962; A61M 25/0074; A61M 25/0687
USPC ............................................... 623/2.11, 1.11
See application file for complete search history.

(56) References Cited

U.S. PATENT DOCUMENTS

| | | |
|---|---|---|
| 4,700,693 A | 10/1987 | Lia et al. |
| 4,784,636 A | 11/1988 | Rydell |
| 5,011,488 A | 4/1991 | Ginsburg |
| 5,092,839 A | 3/1992 | Kipperman |
| 5,112,304 A | 5/1992 | Barlow et al. |
| 5,501,694 A | 3/1996 | Ressemann et al. |
| 5,549,551 A | 8/1996 | Peacock et al. |
| 5,634,928 A | 6/1997 | Fischell et al. |
| 5,891,056 A | 4/1999 | Ramzipoor |
| 5,916,147 A | 6/1999 | Boury |
| 5,968,069 A | 10/1999 | Dusbabek et al. |
| 6,039,721 A | 3/2000 | Johnson et al. |
| 6,210,370 B1 | 4/2001 | Chi-Sing et al. |
| 6,383,171 B1 | 5/2002 | Gifford et al. |

(Continued)

FOREIGN PATENT DOCUMENTS

| | | |
|---|---|---|
| FR | 2 945 440 A1 | 11/2010 |
| WO | WO 01/51114 A2 | 7/2001 |

(Continued)

OTHER PUBLICATIONS

Appln No. 201280047150.7, Chinese First Office Action and Search Report, Jun. 16, 2015, 16pgs.

*Primary Examiner* — Julian W Woo
*Assistant Examiner* — Shaun L David

(57) ABSTRACT

A catheter assembly according to the present invention includes a handle assembly, an introducer sheath, and a distal tip assembly. The distal tip assembly can include first and second retaining sleeves and a slotted tip with a non-traumatic tip guard positioned at the proximal end of the slotted tip. The handle assembly can include a fixed main handle and two or more rotating handles that allow a user to control the distal tip assembly of the catheter. Each control knob on the handle assembly controls a portion of the components on the distal by of the catheter by allowing for precise manipulation of various delivery shafts. Each delivery shaft extends from the handle assembly to respective positions towards the distal end of the catheter.

6 Claims, 10 Drawing Sheets

(56) References Cited

U.S. PATENT DOCUMENTS

| | | | |
|---|---|---|---|
| 6,485,502 B2 | 11/2002 | Don Michael et al. | |
| 6,544,215 B1 | 4/2003 | Bencini et al. | |
| 6,605,056 B2 | 8/2003 | Eidenschink et al. | |
| 6,716,231 B1 | 4/2004 | Rafiee et al. | |
| 6,991,616 B2 | 1/2006 | Bencini et al. | |
| 7,044,958 B2 | 5/2006 | Douk et al. | |
| 7,220,269 B1 | 5/2007 | Ansel et al. | |
| 7,351,255 B2 | 4/2008 | Andreas | |
| 7,374,567 B2 | 5/2008 | Heuser | |
| 7,462,191 B2 * | 12/2008 | Spenser et al. | 623/1.23 |
| 2001/0031981 A1 | 10/2001 | Evans et al. | |
| 2003/0158516 A1 | 8/2003 | Wholey et al. | |
| 2004/0092870 A1 * | 5/2004 | Squire et al. | 604/103.08 |
| 2004/0092956 A1 | 5/2004 | Liddicoat et al. | |
| 2004/0225322 A1 * | 11/2004 | Garrison et al. | 606/200 |
| 2006/0020327 A1 * | 1/2006 | Lashinski et al. | 623/1.25 |
| 2006/0116750 A1 * | 6/2006 | Hebert et al. | 623/1.11 |
| 2006/0206202 A1 | 9/2006 | Bonhoeffer et al. | |
| 2007/0021686 A1 | 1/2007 | Gellman et al. | |
| 2007/0225681 A1 | 9/2007 | House | |
| 2007/0265637 A1 * | 11/2007 | Andreas et al. | 606/108 |
| 2007/0299502 A1 * | 12/2007 | Hebert et al. | 623/1.11 |
| 2008/0132989 A1 | 6/2008 | Snow et al. | |
| 2008/0255652 A1 | 10/2008 | Thomas et al. | |
| 2009/0018529 A1 | 1/2009 | Hoffman et al. | |
| 2009/0076598 A1 * | 3/2009 | Salahieh et al. | 623/2.11 |
| 2009/0264859 A1 | 10/2009 | Mas | |
| 2009/0281619 A1 | 11/2009 | Le et al. | |
| 2011/0172764 A1 * | 7/2011 | Badhwar | 623/2.11 |
| 2012/0078237 A1 * | 3/2012 | Wang | A61F 2/2436 606/1 |

FOREIGN PATENT DOCUMENTS

| | | |
|---|---|---|
| WO | WO 2004/082530 A2 | 9/2004 |
| WO | WO 2009/137359 | 11/2009 |

* cited by examiner

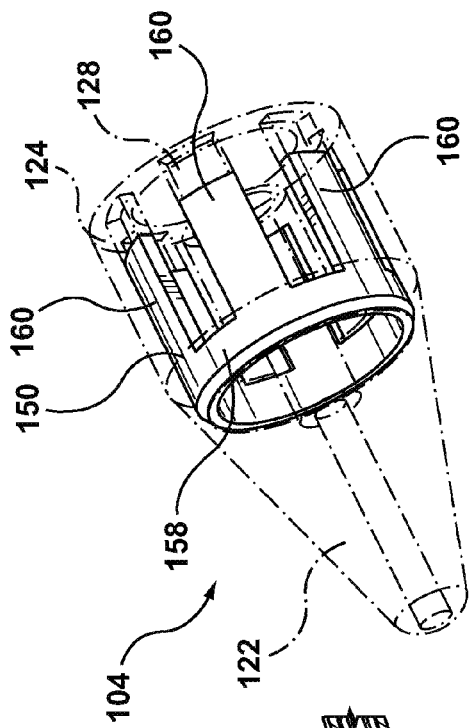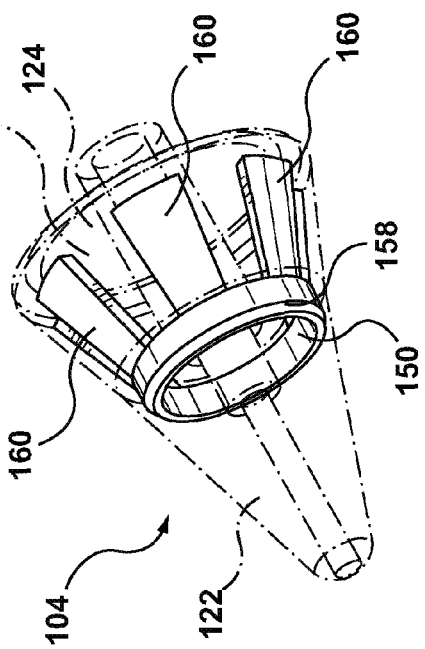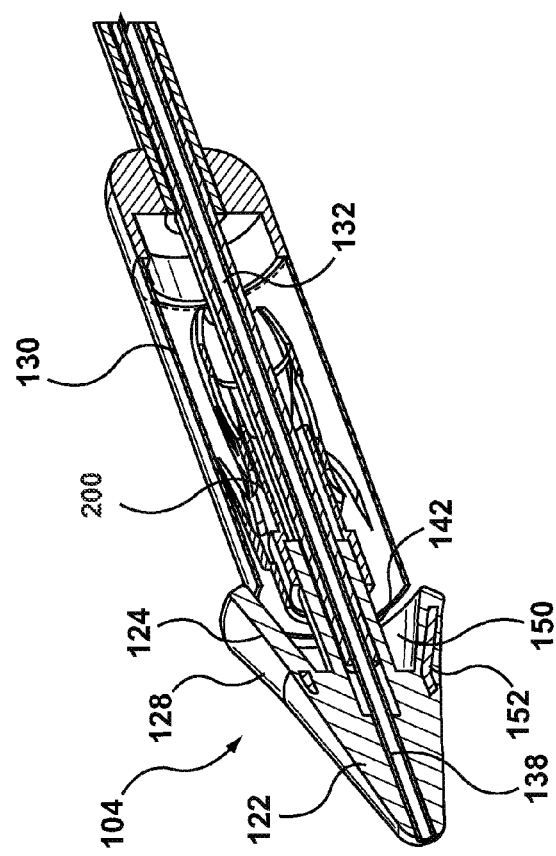

DISTAL TIP ASSEMBLY FOR A HEART VALVE DELIVERY CATHETER

BACKGROUND

Field

The present invention relates to catheters for delivering a prosthesis and, particularly, to delivery catheters having an a traumatic distal tip assembly.

Background

Recently, minimally invasive approaches have been developed to facilitate catheter-based implantation of prostheses, for example, transcatheter aortic-valve prosthesis implantation. Typically, during transcatheter prosthesis implantations, a prosthesis is radially contracted onto a delivery catheter so that the prosthesis can be introduced into a body lumen, for example, into the femoral artery, the brachial artery, or the aorta, or into a body cavity, for example, a chamber of the heart (e.g., the ventricle). The contracted configuration of the prosthesis on the delivery catheter can be maintained by a retaining sleeve positioned over the prosthesis. Using the delivery catheter, the prosthesis can then be guided to the desired implantation site through the body lumen or body cavity. Once the prosthesis is advanced to a desired target site, the prosthesis can be deployed by removing the retaining sleeve and allowing the prosthesis to expand, for example, through balloon expansion or self-expansion.

A delivery catheter sometimes must be navigated through the tortuous anatomy of a body lumen or cavity. As the catheter articulates through the tortuous anatomy, the retaining sleeve can bend. The bending action of the retaining sleeve can cause the distal, leading edge of the retaining sleeve to flex outward (e.g., "fishmouth") from an adjacent distal tip of the delivery catheter, exposing the distal edge. The exposed edge of the retaining sleeve can contact the wall of the body lumen or cavity, which can cause damage to the wall, especially in diseased body lumens. For example, during a trans-femoral delivery of a heart valve prosthesis, the delivery catheter must navigate around the aortic arch, which can cause the retaining sleeve to bend and can expose the retaining sleeve's distal, leading edge. The exposed leading edge of the retaining sleeve may damage the aortic wall if the edge contacts the wall.

Accordingly, there is a need for delivery catheters that have an atraumatic distal tip assembly that can reduce the risk of damage to the walls of the body lumen or cavity that may occur during delivery of a prosthesis to a desired target site.

BRIEF SUMMARY

A catheter for implanting a prosthesis can include a retaining sleeve that defines a hollow cavity. The retaining sleeve can contain a prosthesis. The retaining sleeve has an outer diameter. The catheter can also have a distal tip assembly configured to move axially relative to the retaining sleeve. The distal tip assembly can have a distal portion and a proximal portion. The proximal portion can be configured to move between a contracted position having a first outer diameter and an expanded position having a second outer diameter. The second outer diameter being larger than the outer diameter of the retaining sleeve.

A method of implanting a prosthesis can include inserting a retaining sleeve and a distal tip assembly of a catheter assembly into a body lumen. The retaining sleeve can be positioned over the prosthesis. The retaining sleeve has an outer diameter. The distal tip assembly can have a distal portion and a proximal portion. The method can also include expanding the outer diameter of the proximal portion of the distal tip assembly such that the outer diameter of the proximal portion is larger than the outer diameter of the retaining sleeve.

BRIEF DESCRIPTION OF THE FIGURES

The accompanying drawings, which are incorporated herein and form part of the specification, illustrate the present invention and, together with the description, further serve to explain the principles of the invention and to enable a person skilled in the relevant art(s) to make and use the invention.

FIG. 11 illustrates a cross-sectional view of a distal tip assembly having a biasing member according to an embodiment.

FIG. 12 illustrates the distal tip assembly and the biasing member of FIG. 11 according to an embodiment.

FIG. 13 illustrates the distal tip assembly and the biasing member of FIGS. 11 and 12 according to an embodiment.

DETAILED DESCRIPTION

The following description of prosthesis delivery catheters and methods of delivering and implanting a prosthesis refers to the accompanying figures that illustrate exemplary embodiments. Other embodiments are possible. Modifications can be made to the embodiments described herein without departing from the spirit and scope of the present invention. Therefore, the following detailed description is not meant to be limiting. Further, it would be apparent to one of skill in the art that the systems and methods described below can be implemented in many different embodiments of hardware. Any actual hardware described is not meant to be limiting. The operation and behavior of the systems and methods presented are described with the understanding that modifications and variations of the embodiments are possible given the level of detail presented. For example, the delivery catheter described below can be adapted for use with different types of prostheses, for example, heart valve prostheses, stents, or valves prostheses for areas of the body other than the heart, and for different approaches, for example, transapical, subclavian, brachial, or trans-femoral. One of skill in the art would readily understand how to incorporate the features and structures described herein into catheters intended for other purposes.

Figure 1:
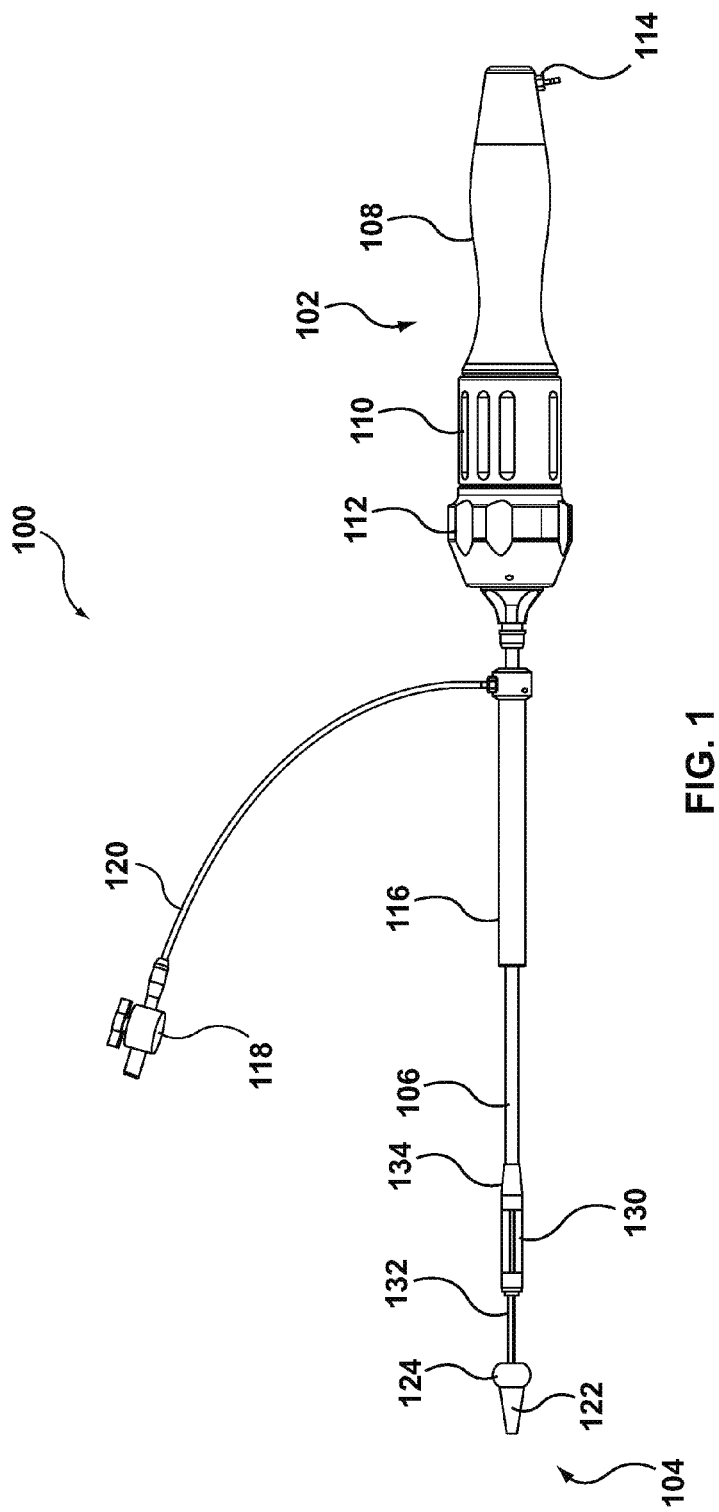
FIG. 1 illustrates a delivery catheter according to an embodiment.

FIG. 1 illustrates a catheter assembly 100 according to an embodiment. Catheter assembly 100 generally includes a handle assembly 102 located at the proximal end of the catheter, a distal tip assembly 104 located at the distal end of the catheter, and an introducer 116 slidably located along an outer delivery shaft 106 extending from handle assembly 102. Outer delivery shaft 106 can be tubular. Outer delivery shaft 106 can be formed of braided material fabricated from, for example, polyethylene naphthalate (PEN), polyester (PET), stainless steel, titanium, nitinol, cobalt nickel alloy, polyamide, polyimide, or the like. In some embodiments, outer delivery shaft 106 can have a degree of flexibility, for example, outer delivery shaft 106 is capable of articulating around a bend in a body lumen while still having sufficient axial strength to prevent buckling during delivery. Other suitable flexible materials can also be used to form outer delivery shaft 106 in other embodiments.

Handle assembly 102 can include a main handle 108, a proximal control knob 110, and a distal control knob 112. Main handle 108, a proximal control knob 110, and distal control knob 112 can be formed of any suitable material. For example, in some embodiments the handle and control knobs are formed of a polymer material. Other materials are possible, as would be understood in the art it is understood that the handle and control knob, for example, need not be made of the same material.

Handle assembly 102 can include a flushing port 114 on main handle 108. Flushing port 114 can, for example, be used to de-air the catheter assembly, to introduce fluid into the native annulus to prevent coagulation and/or thrombosis, to deliver site specific drugs, or to introduce radiopaque fluid into the body.

Catheter assembly 100 can include a flushing tap 118 and a flushing tap lead 120 connected to introducer 116. Introducer 116 can be a tubular member that is slidably located over outer delivery shaft 106. Introducer 116 can be formed of a variety of materials, for example, stainless steel or various polymer materials.

Catheter assembly 100 further includes a prosthesis retaining sleeve 130 and a prosthesis retaining sleeve connector 134. Prosthesis retaining sleeve 130 can be a tubular cylinder that defines a hollow cavity configured to receive a contracted prosthesis, for example, a heart valve prosthesis. Accordingly, prosthesis retaining sleeve 130 maintains the contracted configuration of the prosthesis on the delivery catheter assembly 100. Prosthesis retaining sleeve connector 134 secures prosthesis retaining sleeve 130 to the distal end of outer delivery shaft 106. Outer delivery shaft 106 extends distally from the interior of handle assembly 102 to sleeve connector 134.

Figure 2:
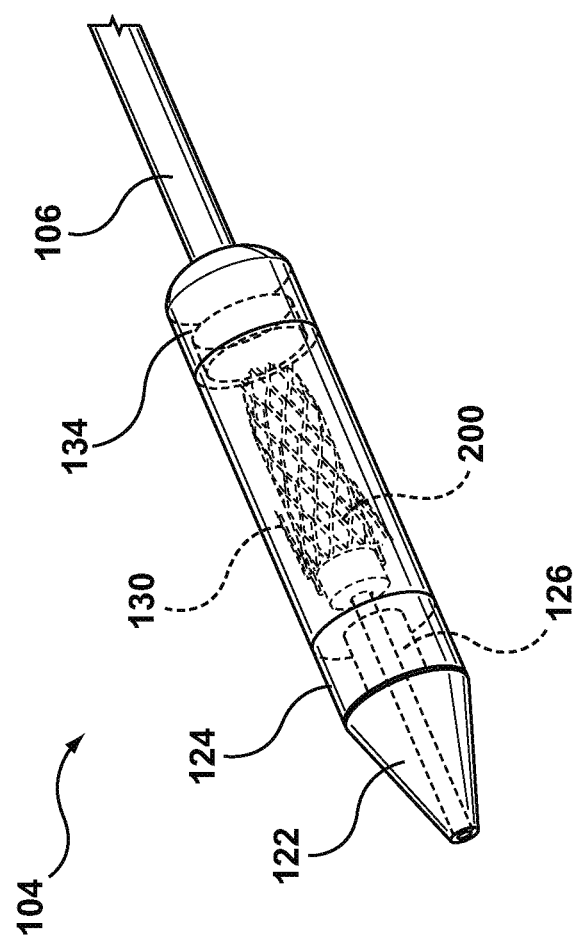
FIG. 2 illustrates a distal tip assembly and a retaining sleeve of a delivery catheter according to an embodiment.

Proximal control knob 110 and distal control knob 112 can be manipulated by a user to control operation of distal tip assembly 104, a prosthesis retaining sleeve 130, or both. In one embodiment, prosthesis retaining sleeve 130 and distal tip assembly 104 are configured to move axially relative to each other. For example, prosthesis retaining sleeve 130 connected to delivery shaft 106 can be advanced proximally, while keeping distal tip assembly 104 stationary, such that prosthesis retaining sleeve 130 moves away from distal tip assembly 104 to an open configuration as shown in FIG. 1. Prosthesis retaining sleeve 130 can be advanced distally, while keeping distal tip assembly 104 stationary, such that the prosthesis retaining sleeve 130 moves towards distal tip assembly 104 until the distal edge of retaining sleeve 130 is adjacent and, in some embodiments, abuts distal tip assembly 104 to a closed configuration (as shown in FIG. 2). Alternatively or conjunctively, distal tip assembly 104 can be configured to move axially in the proximal and distal directions. Accordingly, to move catheter assembly 100 into the open configuration as shown in FIG. 1, distal tip assembly 104 and intermediate delivery shaft 132 to which distal tip assembly 104 is attached can be advanced distally while keeping retaining sleeve 130 stationary. To move catheter assembly 100 into the closed position, distal tip assembly 104 and intermediate delivery shaft 132 can be advanced proximally towards prosthesis retaining sleeve 130.

Distal tip assembly 104 is positioned on and connected to the distal end of intermediate delivery shaft 132. Intermediate delivery shaft 132 extends from the interior of handle assembly 102 to distal tip assembly 104, to which the distal end of intermediate deliver shaft 132 is attached. Intermediate delivery shaft 132 is encompassed by outer delivery shaft 106 from the interior of handle assembly 102 until outer delivery shaft 106 terminates at sleeve connector 134.

Intermediate delivery shaft 132 can be a tubular member, in one embodiment, a guide wire shaft 138 (see, e.g., FIGS. 3 and 8-11) is encompassed within intermediate delivery shaft 132 and extends from the inside of handle assembly 102 to the distal end of distal tip assembly 104. Accordingly, catheter 100 can be configured to be advanced along a guide wire (not shown), for example, a guide wire having a 0.035 inch diameter. However, the dimensions of the catheter components can be adjusted for advancement over guide wires with larger or smaller diameters.

In one embodiment, at least three shafts (for example, delivery shaft 106, intermediate shaft 132, and guide wire shaft 138) extend from handle assembly 102, and the shafts are nested along at least a part of their lengths. Guide wire shaft 138 is encompassed by intermediate delivery shaft 132 from a position inside of handle assembly 102 to a proximal portion 124 of distal tip assembly 104, which can be hollow through at least a portion thereof. Intermediate delivery shaft 132 is connected to, and ends at, proximal portion 124 of distal tip assembly 104. In turn, intermediate delivery shaft 132 is encompassed by outer delivery shaft 106 from a position inside handle assembly 102 to the prosthesis retaining sleeve connector 134. Outer delivery shaft 106 is connected to, and ends at, the retaining sleeve connector 134. Intermediate delivery shaft 132 and guide wire shaft 138 can be constructed of various polymer materials. Persons of ordinary skill in the art would appreciate that the lengths and configurations of introducer 116, delivery shaft 106, intermediate delivery shaft 132, and guide wire shaft 138 can be modified depending on the application.

In one embodiment, distal tip assembly 104 includes a distal portion 122 and proximal portion 124. Distal portion 122 can have any suitable atraumatic shape, for example, a shape that does not have any blunt edges. Atraumatic shapes can include, for example, a semi-spherical shape, a conical shape with a rounded distal tip (as illustrated in FIGS. 1-13), or any other suitable atraumatic shapes. Distal portion 122 can be made of any suitable flexible material, for example, a polymer material, to prevent trauma to the wall of a body lumen or cavity. Distal portion 122 can function as a solid dilator tip, in one embodiment, distal portion 122 cannot expand the outer diameter does not change.

Proximal portion 124 can be configured to move from a contracted position to an expanded position having a larger outer diameter. Proximal portion 124 can have an outer diameter in the expanded position that is larger than an outer diameter of prosthesis retaining sleeve 130. In one embodiment, the outer diameter of proximal portion 124 is larger than the outer diameter of retaining sleeve 130 at its distal edge. In the expanded position, proximal portion 124 can have any suitable profile, for example, an arcuate profile (in which the largest outer diameter occurs at a central portion of proximal portion 124), a straight profile (in which the outer diameter is constant along the entire length of proximal portion 124), or a tapered profile (in which the outer diameter increases as proximal portion 124 extends proximally, for example, such that a proximal end of proximal portion 124 has the largest outer diameter).

FIG. 2 illustrates a distal tip assembly 104 and retaining sleeve 130 according to an embodiment. Retaining sleeve 130 is positioned over prosthesis 200, for example, a heart valve prosthesis. Proximal portion 124 is in a contracted position such that the outer diameter of proximal portion 124 is substantially the same as the outer diameter of prosthesis retaining sleeve 130. Proximal portion 124 can include a balloon element 126. Balloon element 126 can be a flexible member capable of containing a fluid, for example, air or water. Balloon element 126 can be inflated by a change in pressure and, particularly, an increase of pressure on an interior side of balloon element 126. Balloon element 126 can encircle the outer contour of proximal portion 124. As shown in FIG. 2, distal tip assembly 104 and retaining sleeve 130 are in the closed configuration in which proximal portion 124 is adjacent and, in some embodiments, abuts prosthesis retaining sleeve 130.

Figure 3:
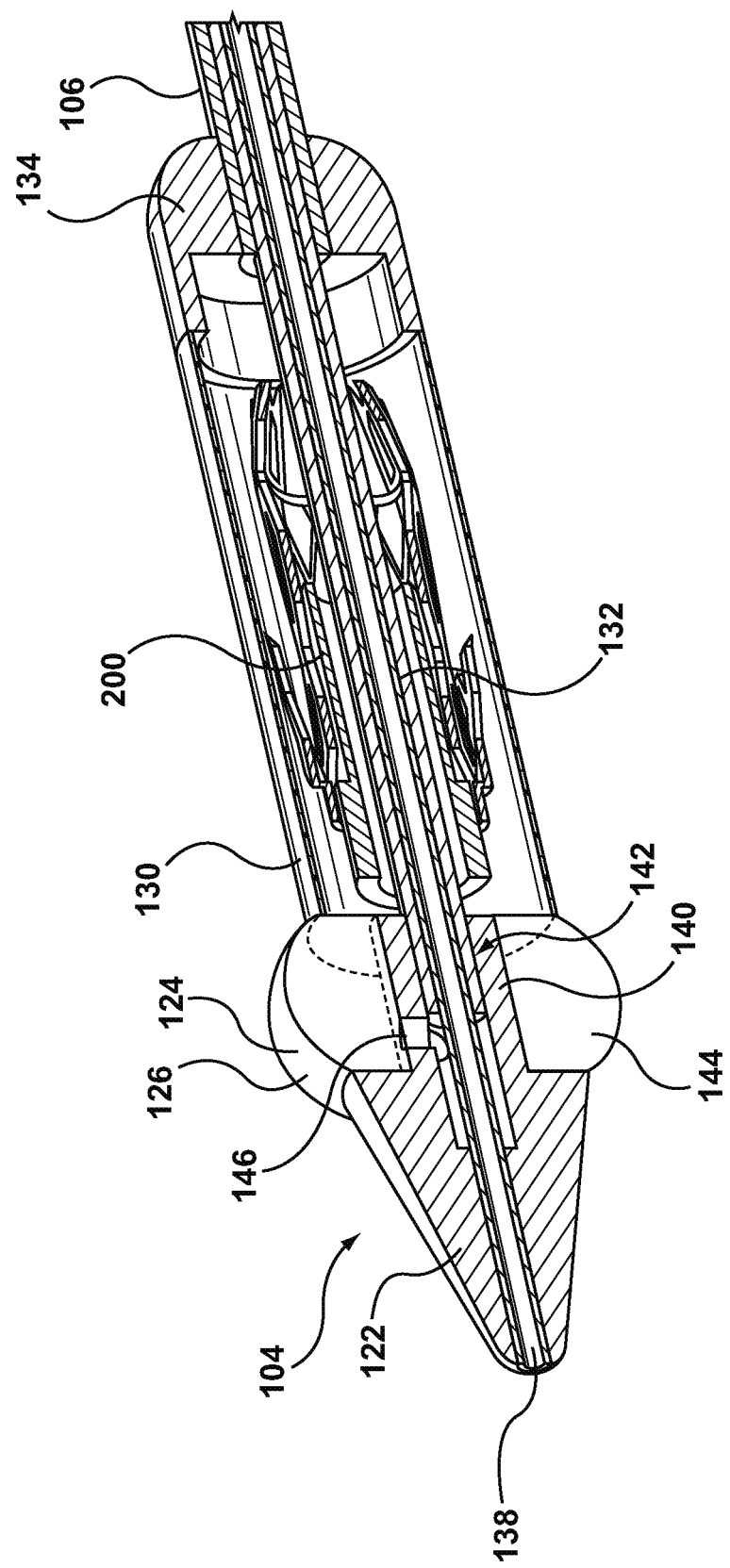
FIG. 3 illustrates a cross-sectional view of the distal tip assembly and the retaining sleeve of FIG. 2 according to an embodiment.

FIG. 3 illustrates distal tip assembly 104 with proximal portion 124 in an expanded position according to an embodiment. Distal tip assembly 104 and retaining sleeve 130 are in the closed configuration such that proximal portion 124 is adjacent to the distal, leading edge of retaining sleeve 130. Proximal portion 124 is in an expanded position such that the outer diameter of proximal portion 124 is larger than the outer diameter of valve retaining sleeve 130. As shown in FIG. 3, proximal portion 124 has an arcuate outer profile. In this position, the enlarged outer diameter of proximal portion 124 provides an atraumatic cushion for the distal edge of retaining sleeve 130 should it flare outward during delivery, for example, while navigating a tortuous bend in a body lumen or cavity. The proximal portion 124 would contact the wall before the edge of retaining sleeve 130 and deflect distal tip assembly 104 and retaining sleeve 130 away from the wall.

Proximal portion 124 includes balloon element 126. Balloon element 126 forms a seal with interior portion 142 and/or distal portion 122 to form outer cavity 140 for receiving a fluid, for example, air or water.

In one embodiment, proximal portion 124 can also include an interior portion 142 that extends proximally from distal portion 122. Interior portion 142 can be cylindrical and can define a center cavity 144. Center cavity 144 can be sized and configured to closely receive intermediate shaft 132, forming a fluid seal. Interior portion 142 can define an aperture 146 in communication with cavity 140 and center cavity 144. Guide wire shaft 138 can be sized and configured such that its outer diameter is spaced apart from the inner diameter of intermediate shaft 132. The gap between guide wire shaft 138 and intermediate shaft 132 can be used as a fluid passage for transferring fluid to or from cavity 140 to change the pressure and, thus, expand or contract balloon element 126.

Figure 4:
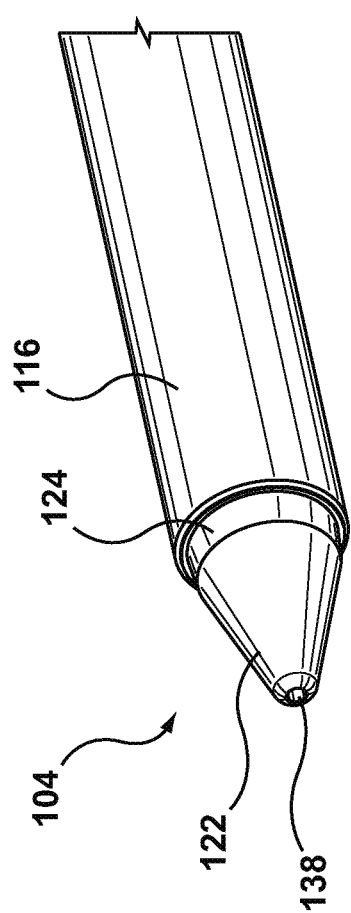
FIG. 4 illustrates a distal tip assembly and an introducer of a delivery catheter according to an embodiment.

FIG. 4 illustrates distal tip assembly 104 and introducer 116 according to an embodiment. Distal tip assembly 104, including proximal portion 124, is within introducer 116. Proximal portion 124 can include a biasing member 152 (see FIG. 5). Biasing member 152 can bias proximal portion 124 outward against introducer 116. In this embodiment, introducer 116 prevents the outer diameter of proximal portion 124 from being significantly greater, if at all, than the outer diameter of retaining sleeve 130.

Figure 5:
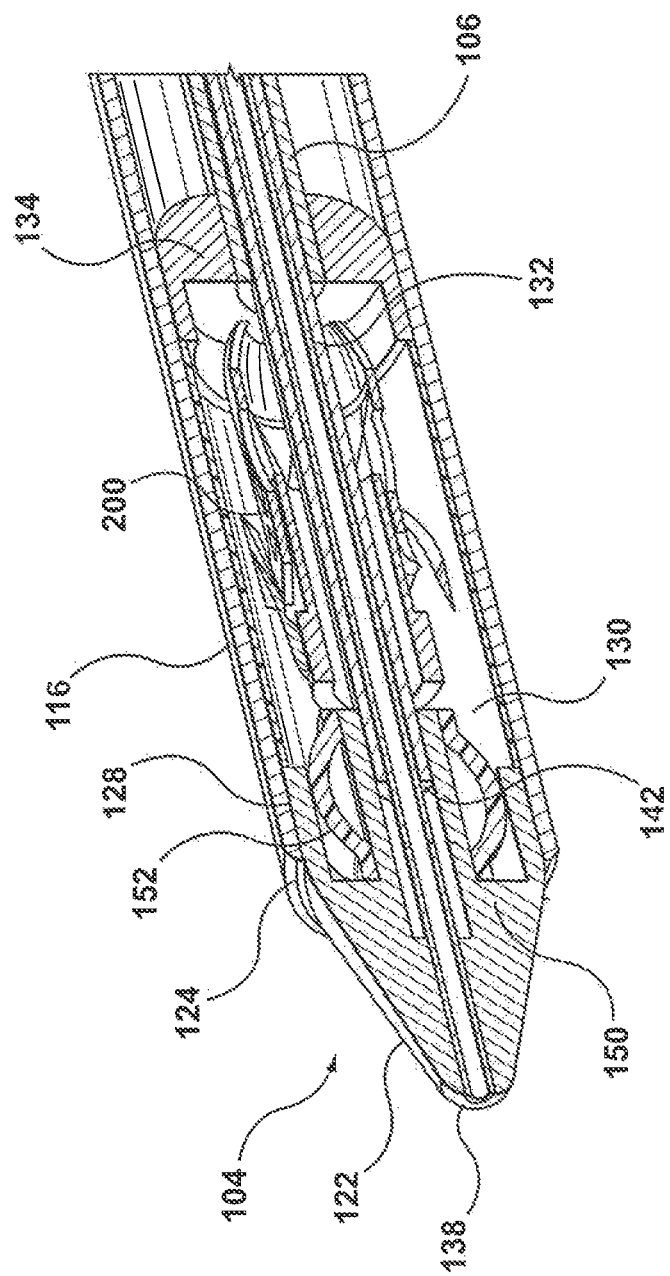
FIG. 5 illustrates a cross-sectional view of the distal tip assembly and the introducer of FIG. 4 according to an embodiment.

FIG. 5 is a cross-sectional view of distal tip assembly 104 according to an embodiment. Proximal portion 124 includes an annular flange 128 that extends proximally from the proximal end of distal portion 122. Annular flange 128 can be flexible, for example, annular flange 128 is capable of bending radially inward or outward with the application of a force. Annular flange 128 can define a chamber 150. Chamber 150 can encircle interior portion 142 of proximal portion 124. Chamber 150 can be configured and arranged to receive biasing member 152. Biasing member 152 has at least one outwardly biased member. In some embodiments, biasing member 152 has more than one outwardly biased member. When seated within chamber 150, biasing member 152 applies an outward force against annular flange 128, biasing annular flange 128 outward against introducer 116. When proximal portion 124 is within introducer 116, proximal portion 124 is in a contracted position with its outer diameter substantially the same as the outer diameter of retaining sleeve 130. In some embodiments (not shown in FIG. 5), annular flange 128 connects with the proximal end of interior support 112 to completely surround biasing member 152.

Figure 6:
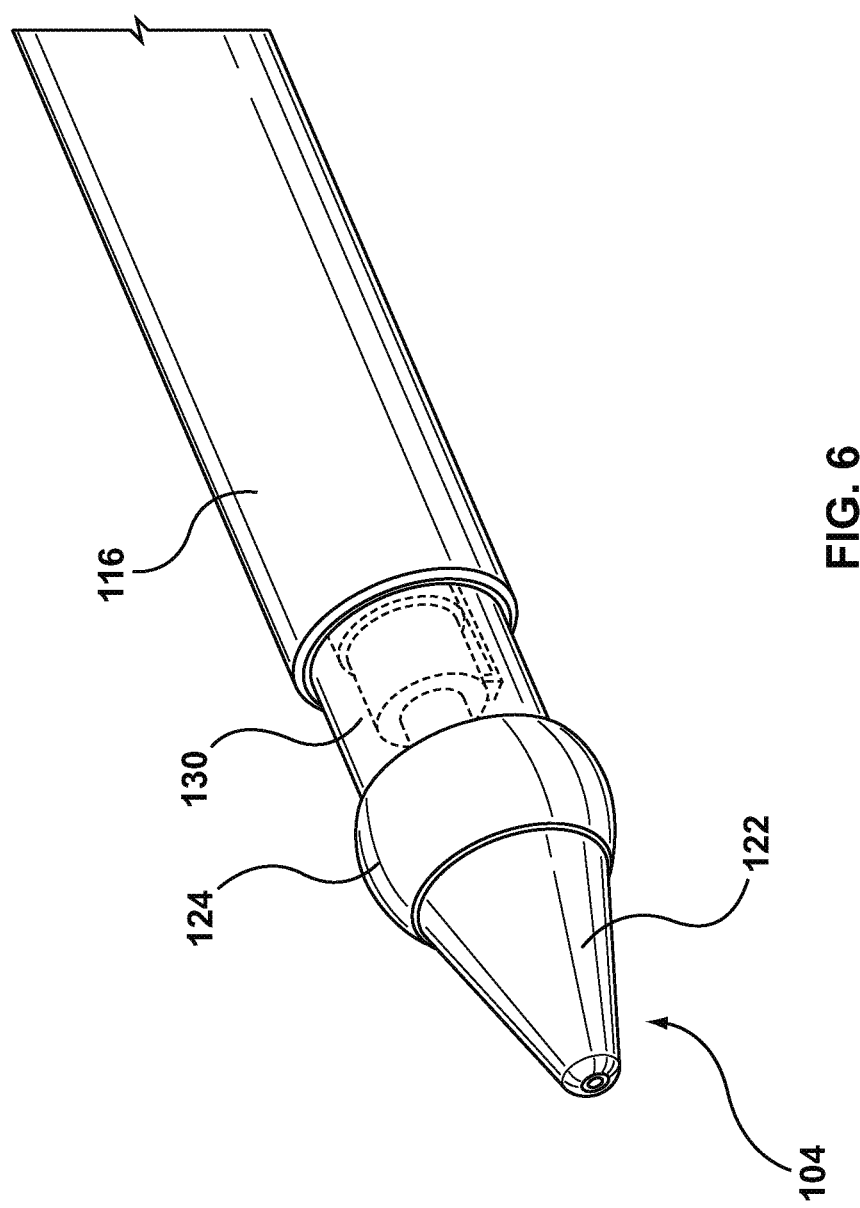
FIG. 6 illustrates the distal tip assembly and the introducer of FIGS. 4 and 5 according to an embodiment.

FIG. 6 illustrates distal tip assembly 104, retaining sleeve 130, and introducer 116 according to an embodiment. The outward biased member(s) of biasing member 152 (not shown) apply an outward force to annular flange 128 (not shown). Accordingly, when proximal portion 124 extends past introducer 116, biasing member 152 causes proximal portion 124 to expand such that its outer diameter is larger than the outer diameter of retaining sleeve 130.

Figure 7:
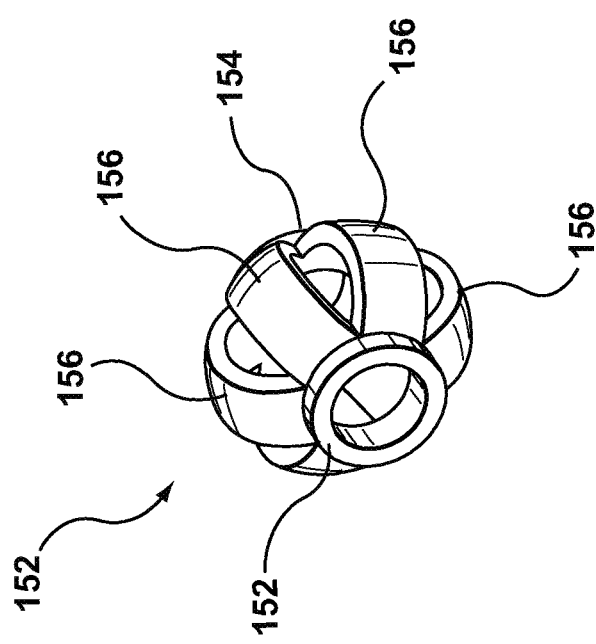
FIG. 7 illustrates a biasing member according to an embodiment.

FIG. 7 depicts biasing member 152 according to an embodiment. Biasing member 152 can be a spring. In one embodiment, biasing member 152 includes a pair of annular rings 154. The outwardly biased member(s) of biasing member 152 can include a plurality of spaced apart leaflets 156 running between the pairs of annular rings 154. Leaflets 156 are biased outward, for example, the center portions of leaflets 156 arc radially outward from annular rings 154. In one embodiment, biasing member 152 can be made of any suitable shape memory material, for example, nitinol. The shape memory material can create the outward bias of leaflets 156 at a certain temperatures, for example, the temperature of blood within the body. In some embodiments, biasing member 152 can be made from other suitable materials, for example, any suitable metal or plastic. In other embodiments, leaflets 156 can have stress concentrations that create the outward bias of biasing member 152.

Figure 8:
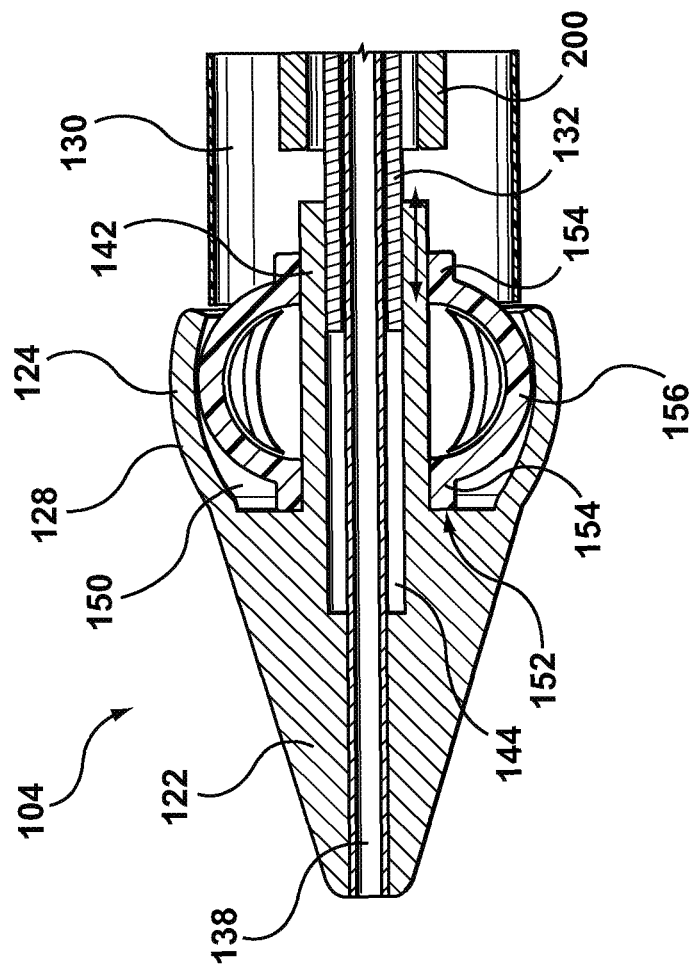
FIG. 8 illustrates a cross-sectional view of the biasing member of FIG. 7 and a distal tip assembly of a delivery catheter according to an embodiment.

FIG. 8 depicts a cross-sectional view of distal tip assembly 104 including biasing member 152 as shown in FIG. 7 according to an embodiment. Biasing member 152 is seated within chamber 150 defined by annular flange 128. As shown in FIG. 8, proximal portion 124 is in an expanded position having an outer diameter greater than the outer diameter of retaining sleeve 130. Proximal portion 124 is adjacent the retaining sleeve 130. Accordingly, the larger diameter of proximal portion 124 provides an atraumatic cushion for the distal edge of retaining sleeve 130 during delivery.

In some embodiments, as shown in FIGS. 5 and 8, biasing member 152 is coupled directly to only interior portion 142 extending proximally from distal portion 122. For example, both annular rings 154 of biasing member 152 are adjacent interior portion 142.

Figure 9:
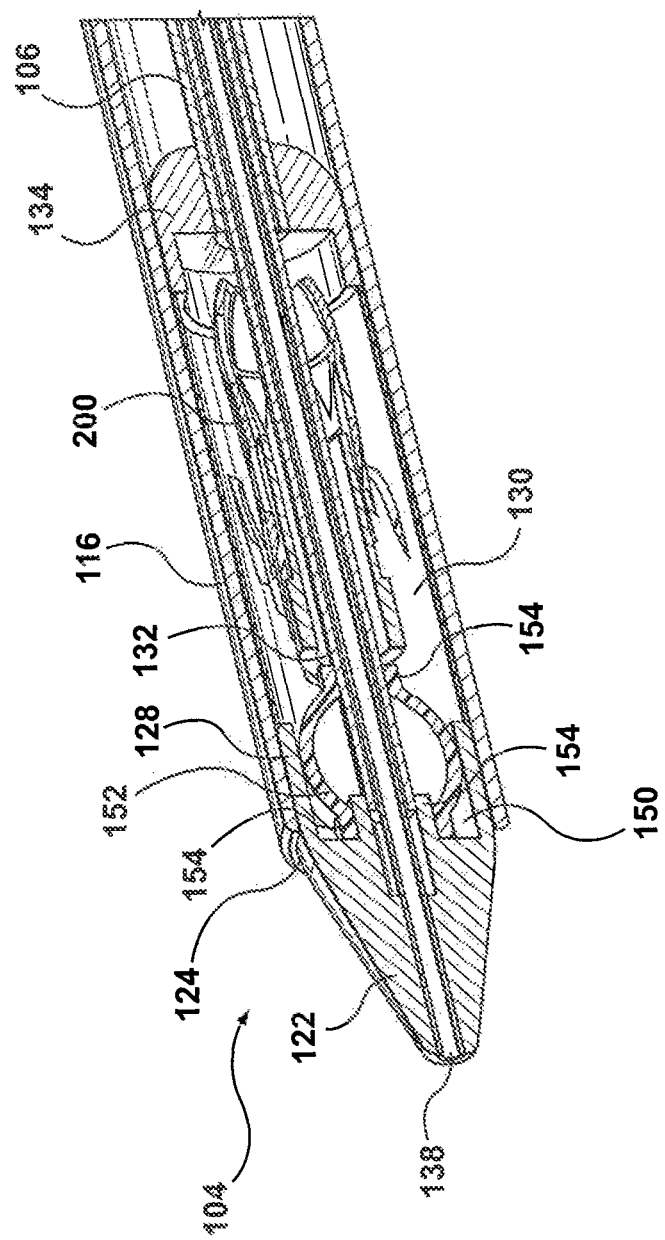
FIG. 9 illustrates a cross-sectional view of a distal tip assembly according to an embodiment.
Figure 10:
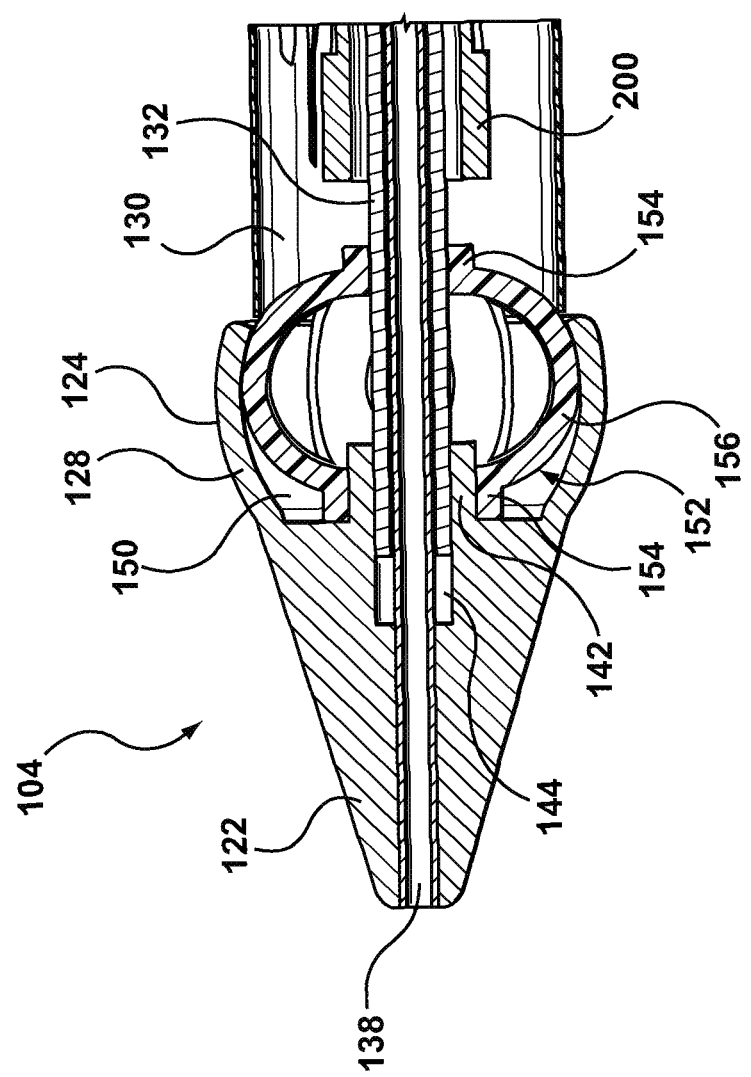
FIG. 10 illustrates an enlarged cross-sectional view of the distal tip assembly of FIG. 9.

In other embodiments, for example, as shown in FIGS. 9 and 10 that illustrate cross-sectional views of distal tip assembly 104 according to an embodiment, a proximal portion of biasing member 152 is coupled directly to intermediate shaft 132, and a distal portion of biasing member 152 is coupled to distal portion 122 and/or interior portion 142. For example, the proximal annular ring 154 is adjacent intermediate shaft 132, and the distal annular ring 154 is adjacent interior portion 142 extending proximally from distal portion 122. Accordingly, adding compression or tension to intermediate shaft 132 can control movement of biasing member 152. Particularly, as intermediate shaft 132 is advanced distally relative to distal portion 122 and interior portion 142, the proximal annular ring 154 attached to intermediate shaft 132 moves distally, causing leaflets 156 to deflect radially outward because the distal annular ring 154 remains stationary relative to distal portion 122 and interior portion 142. As intermediate shaft 132 is advanced proximally relative to distal portion 122 and interior portion 142, the proximal annular ring 154 attached to intermediate shaft 132 moves proximally, causing leaflets 156 to flatten because the distal annular ring 154 remains stationary relative to distal portion 122 and interior portion 142.

FIG. 11 is a cross-sectional view of distal tip assembly 104 and retaining sleeve 130 according to an embodiment. As shown in FIG. 11, the profile of proximal portion 124 in the expanded position is tapered with the outer diameter of proximal portion 124 increasing as proximal portion 124 extends proximally. Thus, the proximal edge of proximal portion 124 has the largest outer diameter. Annular flange 128, and in some embodiments a portion of distal portion 122, can have an over-molded biasing member 152—biasing member 152 is encased by proximal portion 124. Biasing member 152 can having one or more outwardly biased members that cause annular flange 128 of proximal portion 124 to flare radially outward, giving proximal portion 124 a larger diameter than the outer diameter of retaining sleeve 130.

FIGS. 12 and 13 illustrate proximal portion 124 in a contracted position and in an expanded position, respectively, according to an embodiment. Biasing member 152 includes annular ring 158 and a plurality of spaced apart tabs 160 that extend proximally from annular ring 158. Tabs 160 are biased outward, causing flange 128 to flare outward as seen in FIG. 13. Annular ring 158 can be over-molded within proximal portion 124 or both the proximal portion 124 and distal portion 122.

In another embodiment (not shown), annular flange 128 can have a preformed profile having an outer diameter of proximal portion 124 that is larger than the outer diameter of retaining sleeve 130. Accordingly, annular flange 128 can be in the expanded position without biasing member 152.

A method of implanting a prosthesis, for example, a heart valve prosthesis, using a catheter according to an embodiment includes inserting distal tip assembly 104 into a body lumen or cavity, for example, the femoral artery, the aorta, the subclavian artery, the brachial artery, or into a chamber of the heart, for example, the ventricle via a patient's heart apex, as is known in the art. Once within the body lumen or cavity, the proximal portion 124 can be expanded to the expanded position having an outer diameter greater than the outer diameter of retaining sleeve 130. The expanded position of proximal portion 124 creates an atraumatic cushion between the wall of the body lumen and the distal edge of retaining sleeve 130. In the expanded condition, proximal portion 124 will contact the wall of the body lumen or cavity before the distal, leading edge of retaining sleeve 130, which will deflect the leading edge of the retaining sleeve away from the wall. In one embodiment, the proximal portion 124 assumes the expanded position automatically once distal tip assembly 104 passes through introducer 116, for example, when proximal portion 124 includes biasing member 152. In another embodiment, proximal portion 124 is selectively expanded to the expanded position, for example, by increasing the pressure in cavity 140 defined by balloon element 126, or in another embodiment by applying compression or tension to intermediate shaft 132 that is connected to a proximal portion of biasing member 152, deflecting biasing member 152.

After expanding proximal portion 124, distal tip assembly 104 can be advanced to a desired target site. The atraumatic cushion created by the proximal portion 124 in the expanded position reduces the risk of damage to the walls of the body lumen or cavity during advancement, particularly, advancement through a bend. At the target site, prosthesis 200, for example, a heart valve prosthesis, is released from the delivery catheter 100, for example, by moving distal tip assembly 104 and retaining sleeve 130 to the open configuration. In some embodiments, a user rotates the knobs of handle assembly 102 to move distal tip assembly 104 distally relative to retaining sleeve 130 to release prosthesis 200. Prosthesis 200 can then expand against the body lumen or cavity wall to secure prosthesis 200 in place.

After deployment of prosthesis 200, distal tip assembly 104 and introducer 116 can be removed from the body lumen or cavity. In one embodiment, proximal portion 124 is selectively reduced to the contracted position. For example, proximal portion 124 can be selectively reduced by decreasing the pressure within cavity 140 defined by balloon element 126, or by deflecting biasing member 152 through the application of compression or tension to intermediate shaft 132 attached to biasing member 152. Distal tip assembly 104 is then pulled back through prosthesis 200. Distal tip assembly 104 can be withdrawn into introducer 116. The introducer 116 and distal tip assembly 104 are then withdrawn from the body lumen or cavity. In another embodiment, proximal portion 124 is reduced to the contracted position when proximal portion is pulled back through introducer 116.

In some embodiments, prosthesis 200 can be a heart valve prosthesis delivered, for example, through a transapical approach, a subclavian approach, a transfemoral approach, and a brachial approach. Components and methods according to embodiments of the present invention can be used in conjunction with catheters designed for alternate approaches.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein.

It is to be understood that the phraseology or terminology herein is for the purpose of description and not of limitation, such that the terminology or phraseology of the present specification is to be interpreted by the skilled artisan in light of the teachings and guidance. The breadth and scope of the present invention should not be limited by any of the above-described exemplary embodiments, but should be defined only in accordance with the following claims and their equivalents.

What is claimed is:

1. A catheter for implanting a prosthesis, comprising:
a retaining sleeve defining a hollow cavity for containing a prosthesis, the retaining sleeve comprising an outer diameter and a distal edge; and
a distal tip assembly disposed distal of the retaining sleeve and configured to move axially relative to the retaining sleeve, the distal tip assembly comprising,
   a tip component having a tapered distal portion and an interior portion extending proximally from the distal portion, wherein a proximal end of the tapered distal portion radially extends from the interior portion, and
   a separate balloon element attached to the tip component and disposed proximal of the tapered distal portion, wherein the balloon element forms a seal with the proximal end of the distal portion of the tip component and a proximal end of the interior portion of the tip component, the balloon element being configured to move between a contracted position comprising a first outer diameter to an expanded position comprising a second outer diameter, the second outer diameter being larger than the outer diameter of the retaining sleeve,
wherein the first outer diameter of the balloon element in the contracted position is constant along the entire length of the balloon element and substantially equal to the outer diameter of the retaining sleeve,
wherein the retaining sleeve is configured to move relative to the distal tip assembly from a closed configuration in which the retaining sleeve abuts against the balloon element of the distal tip assembly and contains the prosthesis to an open configuration in which the retaining sleeve separates from the balloon element of the distal tip assembly for releasing the prosthesis from the catheter,
wherein when the retaining sleeve is in the closed configuration, the balloon element of the distal tip assembly in each of the contracted position and the expanded position contacts the distal edge of the retaining sleeve.

2. The catheter of claim 1, wherein in the expanded position an outer profile of the balloon element is arcuate.

3. The catheter of claim 1, wherein in the expanded position an outer profile of the balloon element is a substantially circular toroid.

4. The catheter of claim 1, further comprising:
a guidewire shaft defining a first lumen; and
a first delivery shaft defining a second lumen, encompassing the guidewire shaft within the second lumen, and coupled to the interior portion of the tip component of the distal tip assembly,
wherein the interior portion of the tip component of the distal tip assembly defines an aperture in fluid communication with each of a cavity formed by the balloon element, and a space within the second lumen formed between the guidewire shaft and the first delivery shaft.

5. The catheter of claim 4, further comprising a second delivery shaft defining a third lumen and encompassing the first delivery shaft and the guidewire shaft within the third lumen, and coupled to the retaining sleeve.

6. The catheter of claim 1, wherein the distal portion and the interior portion of the tip component of the distal tip assembly are non-expandable.

* * * * *